(12) United States Patent
Aven

(10) Patent No.: US 6,872,736 B1
(45) Date of Patent: Mar. 29, 2005

(54) NON-AQUEOUS EMULSIFIABLE CONCENTRATE FORMULATION

(75) Inventor: Michael Aven, Mainz (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/491,708

(22) Filed: Jan. 26, 2000

(51) Int. Cl.$^7$ ............... A01N 43/64; A01N 43/50; A01N 43/56; A61K 31/41; A61K 31/415

(52) U.S. Cl. ............... 514/359; 514/383; 514/385; 514/403

(58) Field of Search ............... 514/359, 383, 514/385, 403, 272

(56) References Cited

U.S. PATENT DOCUMENTS

| | | |
|---|---|---|
| 4,938,792 A | 7/1990 | Kumazawa et al. |
| 5,393,770 A | 2/1995 | Grayson |
| 5,593,996 A | 1/1997 | Pees et al. |
| 5,679,866 A | 10/1997 | Curtze et al. |
| 5,714,507 A * | 2/1998 | Valcke et al. ............... 514/383 |
| 6,444,618 B1 * | 9/2002 | Aven et al. ............... 504/317 |

FOREIGN PATENT DOCUMENTS

| | | |
|---|---|---|
| EP | 0 351 195 A | 1/1990 |
| EP | 0 933 025 A | 8/1999 |

OTHER PUBLICATIONS

U.S. Appl. No. 08/914,966, filed Aug. 20, 1997, Curtze et al.
U.S. Appl. No. 09/063,199, filed Apr. 20, 1998, Rehnig.
U.S. Appl. No. 09/108,762, filed Jul. 1, 1998, Schmidt et al.

* cited by examiner

Primary Examiner—Alton Pryor

(74) Attorney, Agent, or Firm—Keil & Weinkauf

(57) ABSTRACT

The invention relates to a non-aqueous, emulsifiable concentrate (EC) formulation for crop protection active compounds which comprises (a1) 50 to 300 g/L of at least one azole derivative having a free hydroxy group or a salt or an adduct thereof, preferably a compound of formula I,

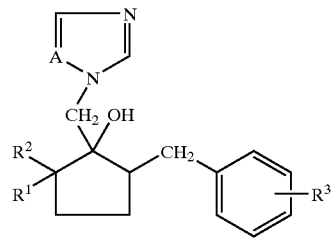

(I)

wherein, $R^1$ and $R^2$ each independently represent hydrogen atom or an optionally substituted alkyl, alkenyl, alkynyl or alkadienyl group;
$R^3$ represents a halogen atom or an optionally substituted alkyl, alkenyl, alkynyl, alkadienyl, alkoxy or aryl group;
A represents a nitrogen atom or a CH group; and
n represents an integer from 0 to 2;

(a2) optionally, 50 to 500 g/L of at least one additional fungicidally active compound;
(b) up to 700 g/L of one or more alkoxylates of an aliphatic alcohol,
(c) up to 100 g/L of one or more non-ionic dispersants,
(d) 10 to 100 g/L of one or more anionic dispersants,
(e) 50 to 600 g/L of one or more polar aprotic organic solvents, and
(f) 150 to 500 g/L of one or more non-polar organic solvents, any
(g) up to 5 g/L of one or more defoamers,
and to the use of such a emulsifiable concentrate as a fungicide.

10 Claims, No Drawings

NON-AQUEOUS EMULSIFIABLE CONCENTRATE FORMULATION

BACKGROUND OF THE INVENTION

The present invention relates to a non-aqueous, emulsifiable concentrate (EC) formulation for fungicidal azole compounds which comprises one or more fungicidal crop protection active compounds, one or more alkoxylates of an aliphatic alcohol, optionally one or more non-ionic dispersants, one or more anionic dispersants, one or more polar aprotic organic solvents, one or more non-polar organic solvents, and optionally one or more defoamers.

Emulsifiable concentrate (EC) formulations conventionally contain an active ingredient, one or more surfactants which act as emulsifiers upon dilution with water and a water immiscible solvent. Typical solvents for conventional EC formulations are aromatic hydrocarbons as for example xylene, Shellsol A or Solvesso 200. These solvents have very low solubilities in water and a high capability of dissolving a wide range of active ingredients.

Due to the presence of the solvent, many fungicides formulated as EC formulations have advantages such a higher degree of systemicity and overall activity compared to the same fungicide formulated as a wettable powder (WP), water dispersible granule (WG) or suspension concentrate (SC).

The observed efficacy of the combination of ingredients can sometimes be significantly higher than that would be expected from the amounts of the individual ingredients used (synergism). The efficacy of the active components can often be improved by addition of other ingredients such as adjuvants.

In order to increase the ease and safety of handling and dosing of these adjuvants by the end-user, and avoid unnecessary packaging material, it is desirable to develop concentrated formulations which already contain such adjuvants.

It is known that the activity of metconazole can be enhanced with certain adjuvants, in particular, with alkoxylated alcohols, as shown, for example, by U.S. Pat. No. 5,393,770.

However, there is no suggestion of concentrated EC formulations comprising metconazole and alkoxylated alcohols.

SUMMARY OF THE INVENTION

Surprisingly, it has been found that stable EC formulations for fungicidal azole compounds having a free hydroxy group, such as bitertanol, cyproconazole, diniconazole, flutriazole, hexaconazole, tebuconazole, triadimenol, trticonazole and uniconazole, and preferably a compound of formula I

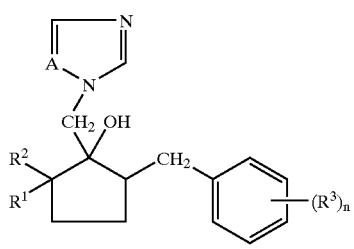

(I)

in which
$R^1$ and $R^2$ each independently represent hydrogen atom or an optionally substituted alkyl, alkenyl, alkynyl or alkadienyl group;
$R^3$ represents a halogen atom or an optionally substituted alkyl, alkenyl, alkynyl, alkadienyl, alkoxy or aryl group;
A represents a nitrogen atom or a CH group; and
n represents an integer from 0 to 2;
or a salt or an adduct thereof;
can be prepared if the formulation comprises, in addition to the compound of formula I, one or more alkoxylates of an aliphatic alcohol, one or more non-polar organic solvents, and at least one polar aprotic organic solvent.

The present invention therefore includes a non-aqueous, emulsifiable concentrate (EC) formulation for fungicidal crop protection active compounds which comprises
(a) (a1) 50 to 300 g/L of at least one azole derivative with a free hydroxy group or a salt or an adduct thereof,
(a2) optionally 50 to 500 g/L of at least one additional fungicidally active compound,
(b) 100 to 700 g/L of one or more alkoxylate of an aliphatic alcohol,
(c) up to 100 g/L of one or more non-ionic dispersants,
(d) 10 to 100 g/l of one or more anionic dispersants,
(e) 50 to 600 g of one or more polar aprotic organic solvents, and
(f) up to 500 g/L of one or more non-polar organic solvents, and
(g) up to 5 g/L of one or more defoamers.

The present invention also includes a method for combating a fungus at a locus which comprises emulsifying a formulation according to the present invention with water and treating said locus with the obtained diluted aqueous formulation.

DETAILED DESCRIPTION OF THE PREFERRED EMBODIMENTS

Preferred fungicidal crop protection compounds are those azoles of formula I, in which
$R^1$ and $R^2$ each independently represent hydrogen atom or an alkyl, group;
$R^3$ represents a halogen atom or an optionally substituted alkyl group;
A represents a nitrogen atom; and
n represents 1; or a salt or an adduct thereof.

Particularly preferred are those compounds of formula I wherein A represents a nitrogen atom; $R^1$ and $R^2$ represent a $C_{1-6}$ alkyl group, preferably a methyl group; and $R^3$ is attached in the para-position and represents a fluoro or chloro atom or a $C_{1-6}$ haloalkyl group.

Most preferred is metconazole, a compound of formula IA,

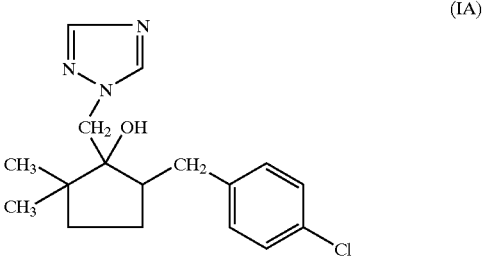

(IA)

which is known from "The Pesticide Manual," 10th Edition, The British Crop Protection Council and The Royal Society of Chemistry, 1994, (hereinbelow abbreviated as "Pesticide Manual"), page 669.

The compound of formula I, due to the basic nature of the azole ring, is capable of forming salts or addition products with inorganic or organic acids or metal ions. The compounds of formula I are preferably used as such in the EC formulation according to the present invention.

The compositions of this invention can be applied to plants or their environment simultaneously with or in succession with other active substances. These other active substances can be either fertilizers, agents which donate trace elements or other preparations which influence plant growth. However, they can also be herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate, together with other substances conventionally used in the art of formulation, such as surfactants or other additives which promote formulation stability.

The other fungicidal compound can be, for example, one which is capable of combating diseases of cereals (e.g. wheat) such as those caused by *Erysiphe, Puccinia, Septoria, Gibberella, Fusarium and Helminthosporium* spp., seed and soil borne diseases and downy and powdery mildews on vines and powdery mildew and scab on apples etc. These mixtures of fungicides can have a broader spectrum of activity than the compound of general formula I alone.

Examples of the other fungicidal compounds are AC 382042, anilazine, azoxystrobin, benalaxyl, benomyl, binapacryl, blasticidin S, Bordeaux mixture, bromuconazole, bupirimate, captafol, captan, carbendazim, carboxin, carpropamid, chlorbenzthiazon, chlorothalonil, chlozolinate, cycloheximide, cymoxanil, cypofuram, cyprodinil, dichlofluanid, dichlone, dichloran, diclobutrazol, diclocymet, diclomezine, diethofencarb, difenoconazole, diflumetorim, dimethirimol, dimethomorph, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fuberidazole, furalaxyl, furametpyr, guazatine, IKF-916, imazalil, iminoctadine, ipconazole, iprodione, isoprothiolane, iprovalicarb, kasugamycin, KH-7281, kitazin P, kresoxim-methyl, mepanipyrim, mepronil, metalaxyl, methfuroxam, MON 65500, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tecloftalame, tecnazene, tetraconazole, thiabendazole, thifluzamide, thiophanate-methyl, thiram, tolclofosmethyl, tolylfluanid, triadimefon, triazbutil, triazoxide, tricyclazole, tridemorph, trifloxystrobin, triflumizole, triforine, validamycin A, vinclozolin, XRD-563 and zarilamid.

In a preferred embodiment of the present invention the EC comprises a mixture of at least one compound of formula I and at least one compound of formula II,

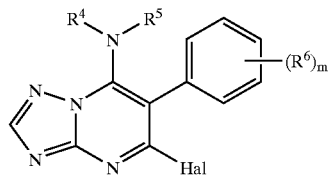

in which
R⁴ and R⁵ each independently represent hydrogen or an optionally substituted alkyl, alkenyl, alkynyl, alkadienyl, haloalkyl, aryl, heteroaryl, cycloalkyl, bicycloalkyl or heterocyclyl group, or
R⁴ and R⁵ together with the interjacent nitrogen atom represent an optionally substituted heterocyclic ring,
R⁶ represents a halogen atom or an alkyl or alkoxy group,
m represents an integer from 0 to 5, and
Hal represents a halogen atom.

The compounds of formula II are known, for example, from U.S. Pat. No. 5,593,996.

Preferred are those compounds of formula II, in which
R⁴ represents an $C_{1-8}$ alkyl, $C_{2-8}$ alkenyl, $C_{3-8}$ cycloalkyl or $C_{1-8}$ haloalkyl group, and R⁵ represents a hydrogen atom or a $C_{5-7}$ alkyl group; or
R⁴ and R⁵ together with the interjacent nitrogen atom represent a $C_{5-7}$ heterocyclic ring being optionally substituted by one or two $C_{1-4}$alkyl groups,
R⁶ independently represent a fluorine or chlorine atom or a methoxy group,
m represents an integer from 2 or 3, and
Hal represents a chlorine atom.

Most preferred is 5-chloro-6-(2,4,6-trifluorophenyl)-7-[2-(1,1,1-trifluoro)propylamino]-[1,2,4]triazolo[1,5-a]pyrimidine, coded as "azolopyrimidine IIA" hereinbelow.

In another preferred embodiment of the present invention the EC comprises a mixture of at least one compound of formula I and at least one compound of formula III,

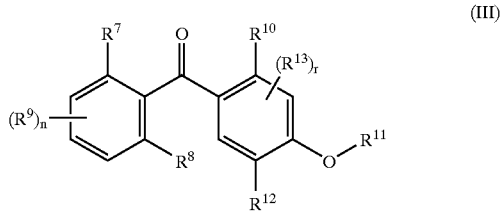

wherein
R⁷ represents a halogen atom, an optionally substituted alkyl, alkanoyloxy or alkoxy group; or a hydroxy group,
R⁸ represents a halogen atom or an optionally substituted alkyl group,
n is 0 or an integer of 1 to 3;
R⁹ independently represents a halogen atom, an optionally substituted alkyl or alkoxy group or a nitro group;
R¹⁰ represents a halogen atom, a cyano, carboxy, hydroxy or nitro group or an optionally substituted alkyl, alkoxy, alkenyl, alkylthio, alkylsulphinyl, alkylsulphonyl or amino group;
R¹¹ represents an optionally substituted alkyl group;
R¹² represents a halogen atom or a nitro group, an optionally substituted alkyl, alkoxy, alkenyloxy, alkynyloxy, alkylthio, cycloalkyl, cycloalkyloxy, aryloxy group;
r is 0, 1 or 2; and
R¹³ independently represents a halogen atom, an optionally substituted alkyl, alkenyl, alkynyl, alkoxy, alkenyloxy, alkynyloxy, cycloalkyl, cycloalkoxy group.

Preferred are those compounds of formula III, in which
R⁷ represents a halogen atom, an alkyl or alkoxy group;
R⁸ represents a halogen atom or an alkyl group,
n is 1;
R⁹ is attached in the ortho-position with respect to R⁸ and represents a halogen atom,
R¹⁰ represents an alkyl group;
R¹¹ represents an alkyl group;
R¹² and R¹³ independently represent an alkoxy group or a benzyloxy group, in which the phenyl ring may be substituted by one or more halogen atoms or alkyl or alkoxy groups; and r represents 1; and $R^{13}$ is attached to the ortho-position with respect to $R^{12}$.

Most preferred is 3-bromo-2,2'-dimethyl-4',5',6,6'-tetramethoxybenzophenone coded benzoylbenzene IIIA.

The compounds of formula III are known, for example, from U.S. Pat. No. 5,679,866.

The compounds of formula I exhibit an extraordinary efficacy against a broad range of phytopathogenic fungi, in particular against fungi from the classes Ascomycetes, Basidiomycetes, Phycomycetes and Deuteromycetes. They are systemic and may be applied as a leaf or soil fungicide.

The formulation according to the invention may be preferably applied for controlling the following phytopathogenic fungal species of the genera: *Alternaria, Botrytis, Cercospora, Colletotrichum, Erysiphe (Blumeria), Elsinoe, Fusarium, Gibberella, Guignardia, Helminthosporium, Hemileia, Monilinia, Mycosphaerella, Nectria, Phythium, Phytophthora, Plasmopara, Podosphaera, Pseudocercosporella, Pseudoperonospora, Puccinia, Pyrenophora, Pyricularia, Rhizoctonia, Sclerotinia, Sclerotium, Septoria, Sphaerotheca, Tilletia, Typhula, Uncinula, Uromyces, Ustilago, Venturia, Verticillum* and others.

The application rate of the compound of formula I according to this invention is usually in the range of 1 to 500 grams of active ingredient (g a.i.) per hectare (h), with rates between 15 to 200 g a.i./ha generally achieving satisfactory control. The optimal rate for a specific application will depend on the crop(s) under cultivation and the predominant species of infesting fungus, and readily may be determined by established biological tests known to those skilled in the art.

The alkoxylates of aliphatic alcohols (b) are preferably liquid, semi-solid, waxy or solid polyalkoxylated aliphatic alcohols. These adjuvants are, as a rule, obtainable by alkoxylation of fatty alcohols having 5–20, preferably 7–19, and, in particular 9–14, C-atoms with an alkyleneoxide having 2–6, preferably 2–3 C-atoms, in particular, with a mixture of ethylenoxide and propyleneoxide. The aliphatic moieties of the said fatty alcohols and amines may be straight-chained or branched. Preferably these compounds correspond to mixed random or block oligomers of the following formula

in which
the average of the indexes given is as follows:
n is an integer from 5 to 20, in particular, 7 to 19;
x is an integer from 1 to 20, in particular, 4 to 10; and
the sum of y and z is an integer from 0 to 12, in particular, 0 to 10.

Of particular interest are those polyalkoxylated aliphatic alcohols which are liquids at temperatures down to at least 20° C. having a viscosity of 30 to 100, in particular 50 to 80 mPa·s at 25° C. The compounds which are commercially available under the trademark Synperonic® and certain Atplus®-types (both sold by Uniqema, formerly ICI Surfactants), in particular, Synperonic® 91-6 and Atplus® MBA 11-7, have been proven to be especially advantageous.

In preferred embodiment of the present invention the non-ionic dispersant (c) is triglyceride, a polyoxyalkylene fatty acid or a polyoxyalkylene alkyl phenol. These dispersants, are as a rule, obtainable by alkoxylation of triglycerides, fatty acids or phenols. The alkoxylation of triglycerides results in mixtures of compounds with one to three glyceride side chains having 9–24, preferably 12–22, and, in particular 14–20, C-atoms, in particular with ethyl-eneoxide. The aliphatic moieties of the said triglycerides may be straight-chained or branched. Preferably, these compounds correspond to mixed oligomers resulting from the alkoxylation of castor or canola oil.

Further preferred dipersants (c) are, for example, Arkopal®-type alkylarylethoxylates (sold by Clariant GmbH, formerly Hoechst AG).

Other particularly preferred dispersants (c) are a castor oil ethoxylates, for example, Ukanil® 2507, which is commercially available from Uniqema, and a canola oil alkoxylate, for example, Eumulgin CO3522, which is commercially available from Henkel KGaA.

Still further preferred dispersants (c) are are polyethyleneoxide-polypropyleneoxide block-copolymers, as for example, Pluronic®-type block-copolymers, which are available from BASF AG.

The anionic dispersants (d) are, as a rule, an alkali or earth alkali sulfonate, which includes also highly concentrated mixtures of such an alkali or earth alkali sulfonates with an organic diluent such as an alcohol, preferably, butanol or 2-ethylhexanol or aromatic hydrocarbons, preferably Solvesso® 200. Such a mixture preferably consists of 40 to 90 wt-% of at least one alkali or earth alkali sulfonate and 10 to 60 wt-% of an organic diluent. Ammonium, alkali and earth alkali alkylbenzene sulfonates are preferred, in particular, calcium dodecylbenzene sulfonates such as Rhodocal® 70/B (Rhodia, formerly Rhône-Poulenc), Phenylsulfonat CA100 (Clariant GmbH) or isopropylammonium dodecyl benzene sulfonate such as Atlox® 3300B (Uniqema).

Preferred polar aprotic solvents (e) can be compounds which are immiscible with water (e1) and have a dielectricity constant of at least 15 at 25° C. Particularly preferred are N-alkylpyrrolidones such as N-octylpyrrolidone or alkyl lactates.

Another group of polar aprotic solvents (e) are compounds which are water-miscible (e2) and have a dielectricity constant of at least 15 at 25° C. Preferred are lactones such as γ-butyrolactone, ketones such as cyclohexanone, and N-cyclohexylpyrrolidone.

The solvent (f) is, as a rule, a water immiscible solvent in which the solubility of the crop protection compound (a) is greater than 5 g/L. Preferably (f is a nonpolar organic solvent selected from the group consisting of aromatic hydrocarbons, aliphatic hydrocarbons, glycols and plant oil esters or mixtures thereof. Preferred aromatic hydrocarbons are, e.g., toulene, xylenes, or substituted naphthalenes, as for example, solventnaphtha, Solvesso® (Deutsche Exxon Chemicals) or Shellsol® A (Deutsche Shell AG). Preferred aliphatic hydrocarbons are, e.g. cyclohexane, paraffins as, for example, Isopar® H (Deutsche Exxon Chemicals) or Shellsol® T (Deutsche Shell AG), preferred plant oil esters are methylated coconut or soybean oil esters, in particular, methyl caprylate such as Witconol 1095 (Witco Corp.), preferred glycols are monoalkyl and dialkyl dialkyleneglycols, in particular dimethyl diethyleneglycol (Diglyme), diethyl diethyleneglycol (Ethyl Diglyme) and monopropyl dipropyleneglycol such as Dowanol® DPNP Glycol Ether (Dow Chemical Company Ltd.). Mixtures of different liquids are often suitable.

Preferred anti-foam agents (g) are silica and polydialkylsiloxanes, in particular, polydimethylsiloxanes or mixtures thereof, such as Rhodorsil® 416 or Rhodosil® 454 from Rhodia, fluoroaliphatic esters such as Fluorad® FC-430 from 3M or perfluoroalkylphosphonic/ perfluoroalkylphosphinc acids or the salts thereof such as Fluowet® PL80, or Fluowet® PP from Clariant. Particularly preferred is a combination of polydimethylsiloxanes and perfluoroalkylphosphonic/perfluoroalkylphosphinc acids.

Preferred are EC formulations comprising:
- (a1) 50 to 300 g/L of metconazole
- (a2) optionally, 50 to 300 g/L of at least one additional fungicidally active compound selected from the formulae II and III;
- (b) 100 to 700 g/L of one or more alkoxylate of an aliphatic alcohol, preferably, a $C_{5-20}$ alcohol alkoxylated with one to nine $C_{2-6}$ alkoxy groups;
- (c) up to 100 g/L of a non-ionic dispersant, preferably, a polyoxyethylene fatty acid,
- (d) 10 to 100 g/L of an anionic dispersant, in particular an amino sulfonate or an alkali or earth alkali sulfonate,
- (e) 50 to 600 g/L of one or more polar aprotic organic solvents, preferably, selected from the group consisting of N—$C_{2-16}$ alkylpyrrolidones, N-cycloalkylpyrollidines, N-hydroxyalkyl-pyrrolidones and lactones; and
- (f) 160 to 500 g/L of one or more non-polar organic solvents, preferably, selected from the group consisting of diethylenglycol dialkylethers, aromatic hydrocarbons and aliphatic hydrocarbons or mixtures thereof;
- (g) up to 5 g/L of a defoamer; preferably, a perfluoroalkyl phosphonic acid, a perfluoroalkyl phosphinic acid or a mixture thereof.

In a particularly preferred embodiment of this invention the EC formulation consists essentially of 50 to 250 g/L, preferably 20 to 100 g/L of an azole derivative of formula I, most preferably, metconazole;

up to 200 g/L, preferably 20 to 150 g/L of a second fungicidal compound agent, most preferably, a compound of formula II or III;

150 to 500 g/L, preferably 200 to 450 g/L of one or two alkoxylates of an aliphatic alcohol, most preferably, a $C_{7-19}$ alcohol being alkoxylated with 4 to 10 ethoxy groups;

0 to 75 g/L, preferably 0 to 50 g/L of an ethoxylated fatty acid or phenol, most preferably, castor oil ethoxylate or nonylphenol ethoxylate;

5 to 100 g/L, preferably 10 to 75 g/L of an alkylbenzene sulfonate, most preferably, ammonium, potassium or sodium dodecylbenzene sulfonate;

100 to 500 g/L, preferably 120 to 480 g/L of a n—$C_{2-12}$ alkylpyrrolidone, most preferably, n-octylpyrrolidone, or γ-butyrolactone;

150 to 500 g/L, preferably 200 to 450 g/L of an non-polar organic solvent, most preferably, selected from the group consisting of diethylenglycol dialkylethers, aromatic hydrocarbons and aliphatic hydrocarbons or mixtures thereof;

up to 5 g/L, preferably 0.5 to 2 g/L of a defoamer selected from perfluoroalkyl phosphonic acids, perfluoroalkyl phosphinic acids and mixtures thereof;

up to 2 g/L of a silicone-based defoamer.

A method of making such a composition is also provided which comprises bringing a compound of formula I into association with the ingredients (b) to (g). It is also envisaged that different isomers or mixtures of isomers of formula I may have different levels or spectra of activity and thus compositions may comprise individual isomers or mixtures of isomers.

Pesticidal compositions are often formulated and transported in a concentrated form which is subsequently diluted by the user before application.

The compositions of the invention may contain 0 to 10% w/v of additives besides (b) to (f) such as corrosion inhibitors, stabilizers, penetrants and stickers. Certain organic solids or inorganic salts may be present dissolved in the formulation to assist in preventing sedimentation and crystallization.

Aqueous emulsions, for example, compositions obtained by diluting the EC formulated product according to the invention with water, also lie within the scope of the invention.

As a commodity, the compositions are in a concentrated form, whereas the end user generally employs diluted compositions. The compositions may be diluted to a concentration down to 0.001% of active ingredient. The doses usually, are in the range from 0.001 to 10 kg a.i./ha, preferably 0.03 to 0.5 kg a.i./ha, and most preferably, 0.04 to 0.4 kg a.i./ha.

For a clearer understanding of the invention, specific examples are set forth below. These examples are merely illustrations and are not to be understood as limiting the scope and underlying principles of the invention in any way. Indeed, various modifications of the invention in addition to those shown and described herein will become apparent to those skilled in the art from the following examples and foregoing description. Such modifications are also intended to fall within the scope of the appended claims.

EXAMPLES

Examples of formulations according to the invention are shown in the following examples A to M:

Identity of Ingredients used in Examples

| Name | Identity |
| --- | --- |
| Metconazole | Fungicidal azole of formula IA |
| Azolopyrimidine IIA | Fungicidal triazolopyrimidine of formula II |
| Benzoylbenzene IIIA | Fungicidal benzoylbenzene of formula III |
| Synperonic ® 91-6 (Uniqema) | Alcohol ethoxylate |
| Synperonic ® NP-4 (Uniqema) | Nonylphenol ethoxylate |
| Atplus MBA 11-7 ® (Uniqema) | Monobranched Alcohol ethoxylate |
| Rhodocal ® 70/B (Rhodia) | 70% Calcium Dodecylbenzene sulfonate in butanol |
| Atlox ® 3300B (Uniqema) | Isopropylammonium Dodecylbenzene sulfonate |
| Ukanil ® 2507 (Uniqema) | Castor oil ethoxylate |
| Fluowet ® PL80 (Clariant GmbH) | Mixture of perfluoroalkylphosphonic and perfluoroalkylphosphinic acids |
| Mergital EL33 (Henkel) | Castor oil ethoxylate with 33 EO units |

Examples A and B

All ingredients are weighed into a container and stirred until a homogenous solution is obtained.

| Example A | | Example B | |
| --- | --- | --- | --- |
| Ingredient | Concentration (g/L) | Ingredient | Concentration (g/L) |
| Metconazole | 90 | Metconazole | 90 |
| Atlox 3300B | 50 | Atlox 3300B | 50 |
| Ukanil 2507 | 20 | Ukanil 2507 | 20 |
| Synperonic 91-6 | 480 | Synperonic 91-6 | 480 |
| N-octylpyrrolidone | 200 | N-dodecylpyrrolidone | 200 |
| Solventnaphtha | to 1 liter | Solventnaphtha | to 1 liter |

| Physico-chemical Tests | | |
|---|---|---|
| Phys-chem Tests | Example A | Example B |
| Density | 0.97 g/ml | 0.96 g/ml |
| Flash point | 59° C. | 60° C. |
| Spray dilution 0.5 hours | ok (homogenous, no cream or precipitate) | ok |
| Spray dilution 2 hours | ok | ok |
| Spray dilution 4 hours | ok | ok |
| Spray dilution 24 hours | ok | ok |
| Storage of EC (7 days 0° C.) | no crystals in EC | no crystals in EC |
| Storage of EC (14 days 40° C.) | no crystals in EC, spray dilution as above ok | no crystals in EC, spray dilution as above ok |
| Storage of EC (14 days 54° C.) | no crystals in EC, spray dilution as above ok | no crystals in EC, spray dilution as above ok |

Example C

All ingredients are weighed into a container and stirred until a homogenous solution is obtained.

| Ingredient | Concentration (g/L) |
|---|---|
| Metconazole | 60 |
| Azolopyrimidine IIA | 100 |
| Synperonic 91-6 | 350 |
| Synperonic NP-4 | 50 |
| Rhodocal 70/B | 50 |
| Fluowet PL80 | 1 |
| n-Octylpyrrolidone | to 1 liter |

| Physico-chemical Tests | |
|---|---|
| Phys-chem Tests | Example C |
| Density | 1.01 g/mL |
| Flash point | >83° C. |
| Spray dilution in 100 ml graduated cylinder, self-emulsification checked, followed by 30 inversions, foam judged (0 hour) | good self-emulsification, after inversions no foam |
| Spray dilution 0.5 hours | ok |
| Spray dilution 2 hours | ok |
| Spray dilution 4 hours | ok |

The EC formulation of Example C combines an adjuvant (alcohol ethoxylate) necessary for good performance of metconazole with a polar aprotic solvent (n-octylpyrrolidone) necessary to dissolve 100 g/L of azolopyrimidine IIA in a water immiscible system. It is possible to raise the metconazole concentration above 60 g/l.

Examples D to H

All ingredients are weighed into a container and stirred until a homogenous solution is obtained.

| | Concentration (g/L) Example | | | | |
|---|---|---|---|---|---|
| Ingredient | D | E | F | G | H |
| metconazole | 125 | 125 | 125 | 83 | 83 |
| Benzoylbenzene IIIA | 90 | 90 | 90 | 60 | 60 |
| γ-Butyrolactone | 100 | — | — | — | — |
| Synperonic 91-6 | 300 | 300 | — | — | — |
| Atplus MBA 11-7 | — | — | 300 | — | — |
| Atlox 3300B | — | 50 | 50 | — | — |
| Rhodocal 70/B | 40 | — | — | 50 | 50 |
| Ukanil 2507 | 50 | 30 | 30 | 30 | 30 |
| Fluowet PL80 | 1 | 1 | 1 | — | — |
| N-Cyclohexylpyrrolidone | — | — | — | 240 | 240 |
| N-Octylpyrrolidone | — | 150 | 150 | 240 | 120 |
| Solventnaphtha | 100 | to 1 liter | to 1 liter | to 1 liter | to 1 liter |
| Diethyleneglycol dimethylether | to 1 liter | — | — | — | — |

Diethyleneglycol diethylether can also be used to partially replace diethylengelycol dimethylether to increase the flash point.

| | Physico-chemical tests | | | | |
|---|---|---|---|---|---|
| Phys-chem Tests | Example | | | | |
| | D | E | F | G | H |
| Density (g/ml) | 1.04 | 1.00 | 1.00 | 0.98 | 0.98 |
| Flash point | 55° C. | 54° C. | 60° C. | 54° C. | 52° C. |
| Spray dilution 0.5 h | ok* | ok | ok | ok | ok |
| Spray dilution 1 h | ok | ok | ok | ok | ok |
| Spray dilution 2 h | ok | ok | ok | ok | ok |
| Spray dilution 4 h | ok | ok | ok | ok | ok |
| Spray dilution 20 h | not recorded | not recorded | not recorded | ≈1 ml cream, otherwise ok | ≈1 ml cream, otherwise ok |
| Spray dilution 24 h | some crystals as precipitate | ok, even after 4 days | very few crystals as precipitate | not tested | not tested |
| Storage of EC (7 days 0° C.) | no crystals | crystals, clear | no crystals | no crystals | no crystals |
| Storage of EC (7 days −5° C.) | no crystals | crystals | some crystals | no crystals | no crystals |

*Ok means that the composition is homogenous, there is no cream or precipitate.

The EC formulations of Examples D to H combine an adjuvant (alcohol ethoxylate) necessary for good performance of metconazole with a polar aprotic solvent necessary to dissolve 125 g/l of benzoylbenzene IIIA in a water immiscible system. It is possible to raise the metconazole concentration above 90 g/l.

Example I

An EC formulation is prepared containing:

| Ingredient | Concentration (g/L) |
| --- | --- |
| Metconazole | 90 |
| Benzoylbenzene IIIA | 100 |
| Synperonic 91-6 | 300 |
| Phenylsulfonat CA100 | 30 |
| Mergital EL33 | 60 |
| Fluowet PL80 | 0.5 |
| Rhodorsil 454 | 0.2 |
| Solventnaphtha | 175 |
| γ-Butyrolactone | 170 |
| Solvesso 200 | to 1 L |

The new ECs are biologically very active (much more than ECs without an adjuvant). Most of the spray dilutions (emulsions) are stable despite a high concentration of water miscible substances (Synperonic 91-6, γ-butyrolactone, N-cyclohexylpyrrolidone). The ingredients have a good environmental profile. In the past, adjuvants have typically been added to the spray tank separately from the pesticidal formulation ("tank-mix adjuvant"). The adjuvant in a one-pack formulation is easier to use than as a tank-mix adjuvant.

What is claimed is:

1. A non-aqueous, emulsifiable concentrate (EC) formulation for fungicidal crop protection active compounds which comprises (a1) 50 to 300 g/L of at least one azole derivative having a free hydroxy group or a salt or an adduct thereof;

(a2) optionally 50 to 500 g/L of at least one additional fungicidally active compound;

(b) 100 to 700 g/L of one or more alkoxylates of an aliphatic alcohol, (c) up to 100 g/L of one or more non-ionic dispersants, (d) 10 to 100 g/L of one or more anionic dispersants, (e) 50 to 600 g/L of one or more polar aprotic organic solvents selected from the group consisting of N-alkylpyrrolidones, N-cycloalkylpyrrolidones, N-hydroxyalkyl-pyrrolidones and lactones, (f) up to 500 g/L of one or more non-polar organic solvents, and (g) up to 5 g/L of one or more defoamers.

2. A formulation according to claim 1 wherein component (a1) is a compound of formula I

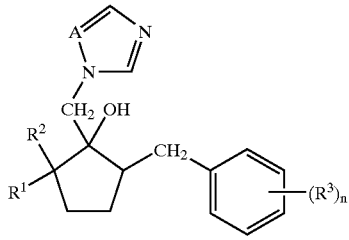

in which

R$^1$ and R$^2$ each independently represent hydrogen atom or an optionally substituted alkyl, alkenyl, alkynyl or alkadienyl group;

R$^3$ represents a halogen atom or an optionally substituted alkyl, alkenyl, alkynyl, alkadienyl, alkoxy or aryl group;

A represents a nitrogen atom or a CH group; and n represents an integer from 0 to 2.

3. A formulation according to claim 1 wherein component (a1) is metconazole.

4. A formulation according to claim 1 wherein said alkoxylate of an aliphatic alcohol (b) is a $C_{5-20}$ alcohol being alkoxylated with 1 to 20 $C_{2-6}$ alkoxy groups.

5. A formulation according to claim 4 wherein said alkoxylate (b) is a straight-chain or branched $C_{7-19}$ alcohol being alkoxylated with 4 to 18 ethoxy and/or propoxy groups, or a mixture thereof.

6. A formulation according to claim 1 wherein the ratio of the crop protection active compounds (a1 and optionally a2) to said alkoxylates of an aliphatic alcohol (b) is between 1:0.5 and 1:100.

7. A formulation according to claim 1 wherein the polar aprotic solvent (e) is immiscible with water.

8. An EC according to claim 1 wherein the de-foamer (g) is selected from perfluoroalkyl-phosphonic acids, per-fluoroalkylphosphinic acids and mixtures thereof, and which additionally comprises a silicone-based defoamer.

9. A method for combating a fungus at a locus which comprises emulsifying a formulation as claimed in claim 1 with water and treating said locus with the obtained diluted aqueous for-mulation.

10. A formulation according to claim 6 wherein the ratio of the crop protection active compounds (a1 and optionally a2) to said alkoxylates of an aliphatic alcohol (b) is between 1:1 and 1:10.

* * * * *